(12) United States Patent
Andrianov et al.

(10) Patent No.: US 11,584,828 B2
(45) Date of Patent: Feb. 21, 2023

(54) POLYPHOSPHAZENE POLYELECTROLYTES AND USES THEREOF

(71) Applicant: University of Maryland, College Park, College Park, MD (US)

(72) Inventors: Alexander K. Andrianov, Gaithersburg, MD (US); Thomas R. Fuerst, Gaithersburg, MD (US); Peter Fusco, Silver Spring, MD (US); Alexander Marin, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 260 days.

(21) Appl. No.: 17/111,043

(22) Filed: Dec. 3, 2020

(65) Prior Publication Data

US 2021/0087342 A1    Mar. 25, 2021

Related U.S. Application Data

(62) Division of application No. 16/314,735, filed as application No. PCT/US2017/040912 on Jul. 6, 2017, now Pat. No. 10,858,483.

(60) Provisional application No. 62/358,879, filed on Jul. 6, 2016.

(51) Int. Cl.
| | | |
|---|---|---|
| *C08G 79/025* | (2016.01) | |
| *A61K 39/39* | (2006.01) | |
| *A61P 37/04* | (2006.01) | |
| *A61P 39/00* | (2006.01) | |

(52) U.S. Cl.
CPC ............ *C08G 79/025* (2013.01); *A61K 39/39* (2013.01); *A61P 37/04* (2018.01)

(58) Field of Classification Search
CPC ......... A61P 37/04; A61K 39/00; A61K 39/39; C08G 79/02; C08G 79/025
See application file for complete search history.

(56) References Cited

U.S. PATENT DOCUMENTS

| | | | |
|---|---|---|---|
| 5,494,673 A | * | 2/1996 | Andrianov ........... A61K 9/1641 424/234.1 |
| 2010/0239611 A1 | | 9/2010 | van Drunen Littel-van den Hurk et al. |
| 2011/0038900 A1 | | 2/2011 | Chakrapani |
| 2016/0008477 A1 | | 1/2016 | Leoni et al. |

FOREIGN PATENT DOCUMENTS

WO      96/40254 A1     12/1996

OTHER PUBLICATIONS

Andrianov, A.K., et al., Poly[di(carboxylatophenoxy)phosphazene] is a potent adjuvant for intradermal immunization, PNAS, Nov. 10, 2009, vol. 106, No. 45, pp. 18936-18941.
Teasdale, I., et al., Polyphosphazenes: Multifunctional, Biodegradable Vehicles for Drug and Gene Delivery, Polymers, Mar. 1, 2013, vol. 5, No. 1, pp. 161-187.

* cited by examiner

*Primary Examiner* — Jeffrey T. Palenik
(74) *Attorney, Agent, or Firm* — Hodgson Russ LLP

(57) ABSTRACT

Polyphosphazenes polyelectrolytes. The polyphosphazenes can be prepared by substituting pendant groups (e.g., ionic groups or pendant groups that can form ionic groups) onto a reactive macromolecular precursor for example, by reaction between the reactive chlorine atoms on the backbone of poly(dichlorophosphazene) and appropriate organic nucleophiles. In certain examples, one or more charged pendant groups of a polyphosphazene is/are further modified to introduce desired counterions, which can be hydrophobic counterions. The polyphosphazenes can activate distinct Toll-Like Receptors (TLRs) and can be used in methods of stimulating an immune response.

12 Claims, 8 Drawing Sheets

POLYPHOSPHAZENE POLYELECTROLYTES AND USES THEREOF

CROSS-REFERENCE TO RELATED APPLICATIONS

This application is a divisional of U.S. patent application Ser. No. 16/314,735, filed on Jan. 2, 2019, which is a National Phase of International Patent Application No. PCT/US2017/040912, filed on Jul. 6, 2017, which claims priority to U.S. Provisional Application No. 62/358,879, filed on Jul. 6, 2016, the disclosures of each of which are incorporated herein by reference.

FIELD OF THE INVENTION

This invention relates to immunotherapies on the basis of polyorganophosphazenes. Specifically, the present invention directs to an agent for the therapeutic or prophylactic treatment of cancer by providing polyphosphazenes capable of synergistic activation of multiple Toll-Like Receptors (TLRs) of the immune system of a mammal. More specifically it directs to polyphosphazene immunotherapeutic agents capable of synergistic activation of TLR7, TLR8, TLR3, or TLR9 of the immune system of a mammal.

BACKGROUND OF THE INVENTION

Toll-like receptors (TLR) serve as pattern recognition receptors for the innate immune system which can be triggered to enhance an adaptive immune response to pathogens [Janeway Jr, C. A. and R. Medzhitov, Innate immune recognition. Annual review of immunology, 2002. 20(1): p. 197-216]. In addition, TLR agonists have been shown to possess anti-tumor activity and can provide synergy in combination [Kaczanowska, S., et al., Journal of leukocyte biology, 2013. 93(6): p. 847-863]. For example, anti-tumor activity has been demonstrated for CpG, a TLR9 agonist, systemically in mice with small tumors [Baines, J. and E. Celis, Clinical Cancer Research, 2003. 9(7): p. 2693-2700]. Anti-tumor synergy has also been demonstrated with TLR3 agonists [Conforti, R., et al., Cancer research, 2010. 70(2): p. 490-500]. However, synergy resulting from the combination of TLR agonists may be required for efficacy against large established tumors. As an example, agonists for TLRs 7, 8, and 9 appear to show greater anti-tumor activity in combination against large tumors in mice, particularly when injected directly in the tumor, as shown for the combination of a TLR7/8 agonist (3M-052) with a CpG TLR9 agonist, eliminating large tumors in mice only when combined [Zhao, G., et al., Journal for immunotherapy of cancer, 2014. 2(1): p. 1].

There exists a need for compound providing stimulating activity with multiple TLRs (poly-TLR agonist).

BRIEF SUMMARY OF THE INVENTION

In an aspect, the present invention provides polyphosphazenes. The polyphosphazenes can be polyelectrolytes. In various examples, a polyphosphazene has the following structure:

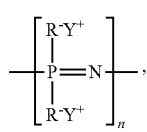

(Structure I)

where $Y^+$ is independently at each occurance in the polyphosphazene is an cationic group selected from the group consisting of $H^+$, $Na^+$, $K^+$, $Ca^{2+}$, protonated spermine groups, protonated spermidine groups, protonated imidazoquinoline groups, (e.g., protonated 1H-imidazo[4,5-c]quinolin-4-aminium groups), protonated substituted imidazoquinoline groups (e.g., protonated substituted 1H-imidazo[4,5-c]quinolin-4-aminium analog groups), protonated thiaimidazoquinoline groups, and protonated substituted thiaimidazoquinoline groups, with the proviso that at least one (e.g., one or both) of the $Y^+$ groups is a protonated imidazoquinoline group, (e.g., 1H-imidazo[4,5-c]quinolin-4-aminium group), protonated substituted imidazoquinoline group (e.g., protonated substituted 1H-imidazo[4,5-c]quinolin-4-aminium analog group), protonated thiaimidazoquinoline groups or protonated substituted thiaimidazoquinoline group, $R^-$ is independently at each occurance in the polyphosphazene an anionic group or group that can be deprotonated to form an anionic group (e.g., carboxylic acid groups, sufonic acid groups, phosphonic acid groups, deprotonated forms thereof), and n is an integer from 10 to 500,000. The protonated groups can be N-protonated and/or S-protonated.

In various examples (e.g., examples of Structure I) one or more $Y^+$ is:

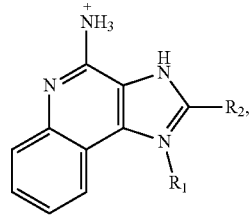

where $R_1$ is independently at each occurance in the polyphosphazene is —H,

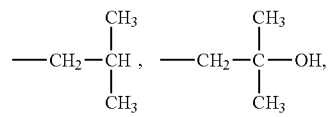

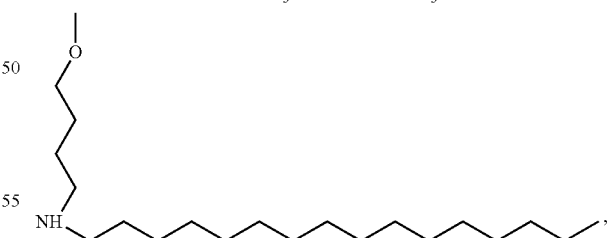

and $R_2$ is independently at each occurance in the polyphosphazene is —H, —$CH_3$, —$CH_2$—$CH_2$—$CH_3$,

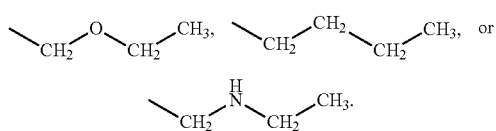

In various examples (e.g., examples of Structure I) one or more Y⁺ is:

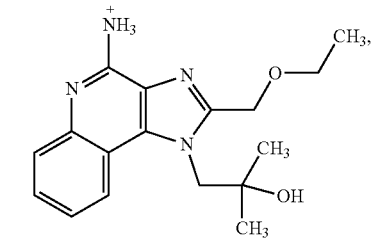

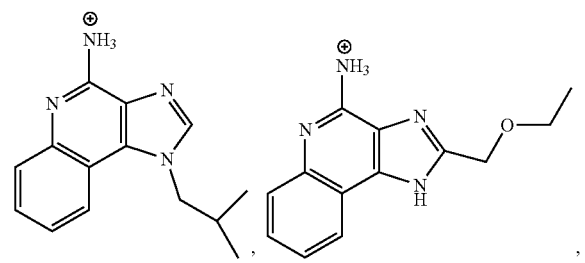

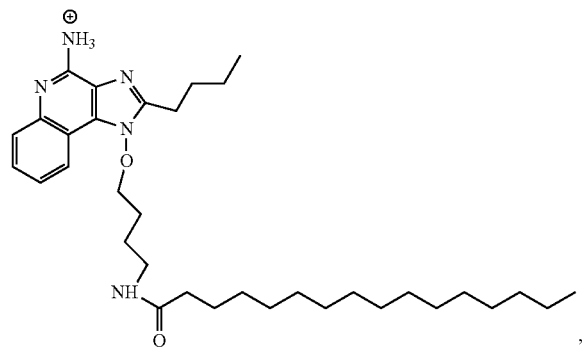

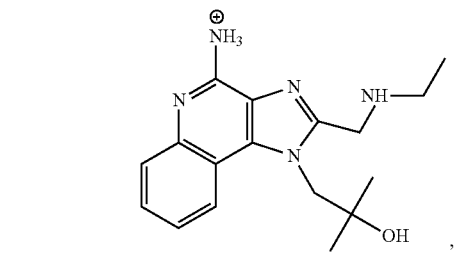

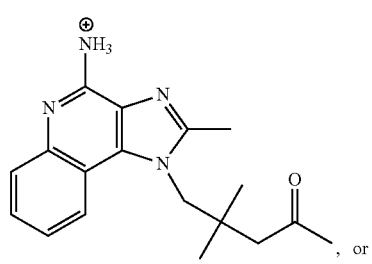, or

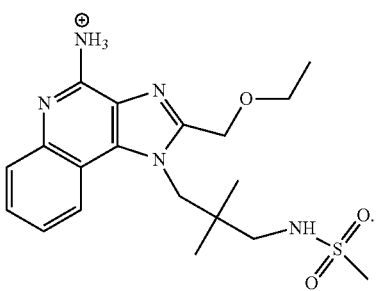

In an example (e.g., of Structure I), the anionic group (e.g., R⁻) is is

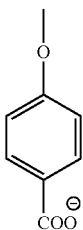

and the counterion (e.g., Y⁺) is

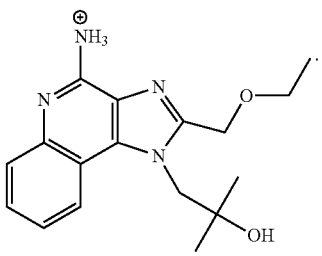 [SMILES: CCOCc1nc2c([NH3+])nc3ccccc3c2n1CC(C)(C)O]

In various examples, a polyphosphazene has the following structure:

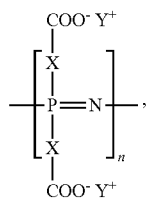

(Structure II)

where X is independently at each occurance in the polymer a linking moiety.

In various examples (e.g., examples of Structure (II)), a linking moiety has independently at each occurance one of the following structures:

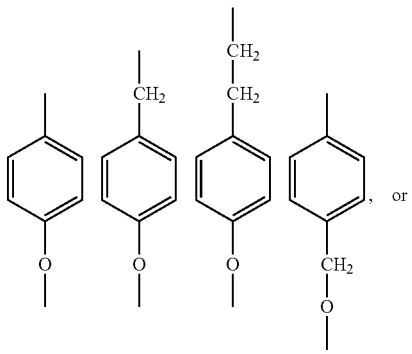

In various examples, the polyphosphazene has one of the following structures:

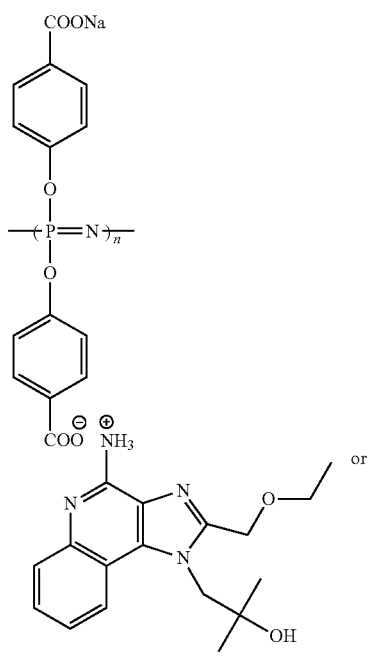

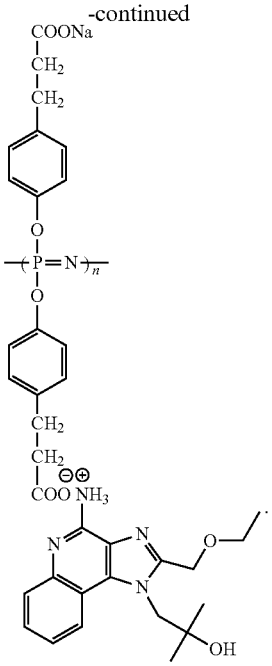

In an aspect, the present invention provides compositions comprising a polyphosphazene of the present invention. In an example, a composition further comprises a pharmaceutically acceptable carrier. In another example, the composition comprises a polyphosphazene, antigen (e.g., vaccine antigen) and, optionally, a pharmaceutically acceptable carrier. In yet another example, the composition comprises a polyphosphazene, an immunomodulating compound and/or TLR agonist, and, optionally, a pharmaceutically acceptable carrier.

In an aspect, the present invention provides methods of stimulating an immune response in an individual comprising administering to an individual a polyphosphazene of the present disclosure (e.g., a polyphosphazene having the following structure:

(Structure I)

$$\left[ \begin{array}{c} R\text{-}Y^+ \\ | \\ P=N \\ | \\ R\text{-}Y^+ \end{array} \right]_n ,$$

where $Y^+$ is independently at each occurance in the polyphosphazene is an cationic group selected from the group consisting of $H^+$, $Na^+$, $K^+$, $Ca^{2+}$, N-protonated spermine group, N-protonated spermidine group, and $R^-$ is independently at each occurance in the polyphosphazene an anionic group, and n is an integer from 10 to 500,000).

In various examples of the methods, one or more Y⁺ is:

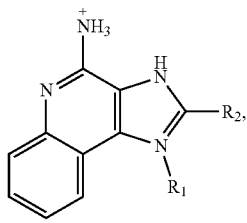

where
R₁ is independently at each occurance in the polyphosphazene is —H,

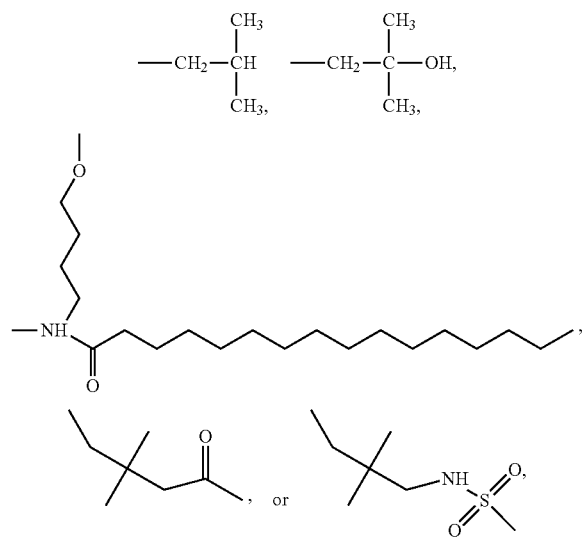

and
R₂ is independently at each occurance in the polyphosphazene is —H, —CH₃ or —CH₂—CH₂—CH₃,

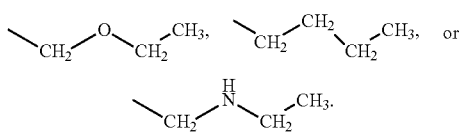

In various examples of the methods, one or more Y⁺ is:

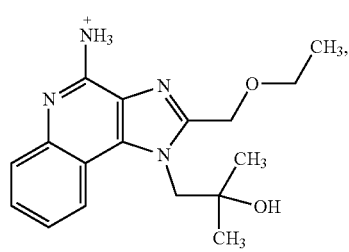

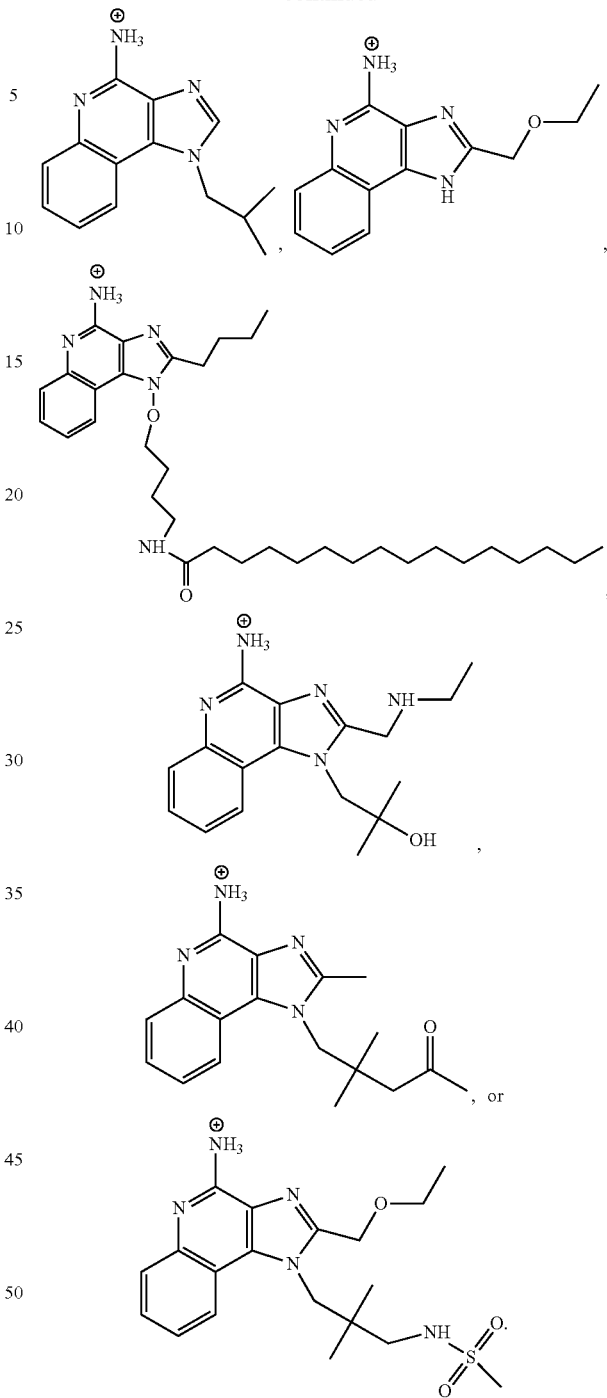

In various examples of the methods, the polyphosphazene is present in (formulated as) a composition (e.g., a composition of the present invention). In an example, the composition comprises a polyphosphazene and a pharmaceutically acceptable carrier. In another example, the composition comprises a polyphosphazene, antigen (e.g., vaccine antigen) and, optionally, a pharmaceutically acceptable carrier. In yet another example, the composition comprises a polyphosphazene, an immunomodulating compound and/or TLR agonist, and, optionally, a pharmaceutically acceptable carrier.

In an example, the stimulating the immune response comprises activating distinct Toll-Like Receptors (TLRs). In an other example, the stimulating the immune response comprises synergistic production tumor necrosis factor alpha (TNF-α).

DETAILED DESCRIPTION OF THE INVENTION

Figure 1:
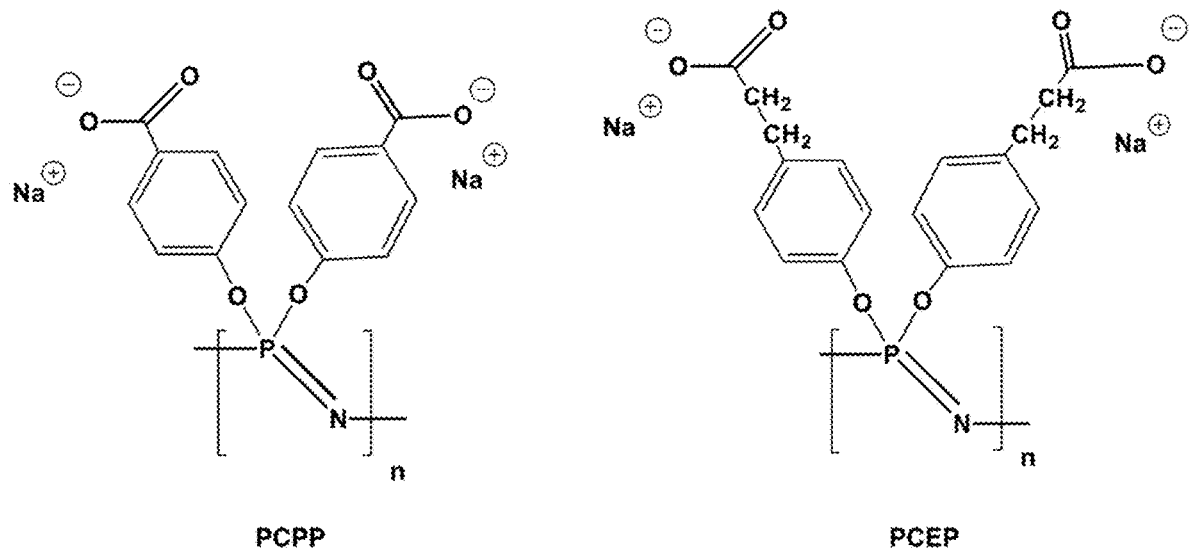
FIG. 1 illustrates chemical structures of PCPP and PCEP.

Although claimed subject matter will be described in terms of certain embodiments and examples, other embodiments and examples, including embodiments and examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present invention provides polyphosphazenes and compositions comprising polyphosphazenes. The polyphosphazenes and compositions can be used in methods of stimulating an immune response in an individual, and in particular can function via activation of multiple, distinct TLRs.

The polyphosphazenes and compositions of the present invention can be used as immunotherapies, which possess antitumor activity. In particular they can be especially effective against large established tumors, for which synergy resulting from the combination of TLR agonists is required. Furthermore, the present invention provides polyphosphazenes and compositions comprising TLR agonists incorporating TLR agonists as counterions to polyphosphazenes.

As used herein, unless otherwise stated, the term "group" refers to a chemical entity that has one terminus that can be covalently bonded to other chemical species or a chemical entity that is charged (e.g., has a charged terminus). Examples of groups include, but are not limited to:

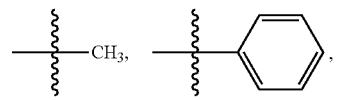

and a protonated spermine molecule.

As used herein, unless otherwise stated, the term "moiety" refers to a chemical entity that has two or more termini that can be covalently bonded to other chemical species. Examples of moieties include, but are not limited to:

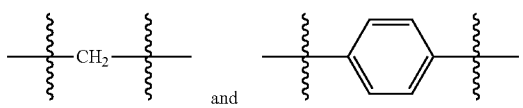

As used herein, unless otherwise indicated, the term "alkaryl" refers to an alkyl-substituted aryl group. A non-limiting example of an alkaryl is an ethylphenyl group.

As used herein, unless otherwise indicated, the term "aralkyl" refers to any group derived from an alkyl group by replacing one or more hydrogen atoms on the alkyl group with one or more aryl groups.

As used herein, unless otherwise indicated, the term "halogen" refers to fluorine atom, chlorine atom, bromine, or iodine atom, and the term "halo" means fluoro group (—F), chloro group (—Cl), bromo group (—Br), and iodo group (—I).

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_{12}$, including all integer numbers of carbons and ranges of numbers of carbons therebetween, alkyl group. The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, and alkynl groups), aryl groups, alkoxide groups, carboxylate groups, carboxylic acids, ether groups, and the like, and combinations thereof.

As used herein, unless otherwise indicated, the term "heteroalkyl" refers to branched or unbranched saturated hydrocarbon groups comprising at least one heteroatom. Examples of suitable heteroatoms include, but are not limited to, nitrogen, oxygen, sulfur, phosphorus, and halogens. The heteroalkyl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof.

As used herein, unless otherwise indicated, the term "alkylamine" refers to branched or unbranched saturated hydrocarbon groups comprising the following structures:

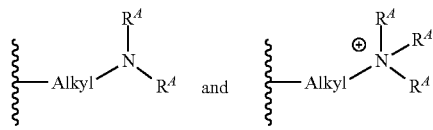

where $R^A$ is hydrogen and where Alkyl is as defined herein.

As used herein, unless otherwise indicated, "aminoalkyl" refers to a

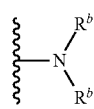

group where each $R^b$ is selected independently from the group consisting of hydrogen atom, substituted or unsubstituted $C_1$ to $C_{12}$, including all integer numbers of carbons and ranges of numbers of carbons therebetween, alkyl chain substituted or unsubstituted phenyl, substituted or unsubstituted heteroaryl, substituted carbonyl, substituted sulfonyl, haloalkyl, and substituted or unsubstituted benzyl groups.

As used herein, unless otherwise indicated, "thioalkyl" refers to a

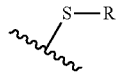

group, where R is selected from a substituted or unsubstituted $C_1$ to $C_{12}$, including all integer numbers of carbons and ranges of numbers of carbons therebetween, alkyl chain substituted or unsubstituted phenyl, substituted or unsubstituted heteroaryl, substituted carbonyl, substituted sulfonyl, haloalkyl, and substituted or unsubstituted benzyl groups.

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups/moieties, alkynyl groups/moieties, and cyclic aliphatic groups/moieties. For example, the aliphatic group can be a $C_1$ to $C_{12}$, including all integer numbers of carbons and ranges of numbers of carbons therebetween, aliphatic group. The aliphatic group can be unsubstituted or substituted with one or more substituent. Examples of substituents include, but are not limited to, various substituents such as, for example, halogens (—F, —Cl, —Br, and —I), additional aliphatic groups (e.g., alkenes, alkynes), aryl groups, alkoxides, carboxylates, carboxylic acids, ether groups, and the like, and combinations thereof.

As used herein, unless otherwise indicated, the term "oxyaliphatic" refers to branched or unbranched hydrocarbon groups containing an oxygen atom and, optionally, degrees of unsaturation. Degrees of unsaturation include, but are not limited to, alkenyl groups/moieties, alkynyl groups/moieties, or cyclic aliphatic groups/moieties. For example, the oxyaliphatic group can be a $C_1$ to $C_{12}$, including all integer numbers of carbons and ranges of numbers of carbons there between, oxyaliphatic group. The oxyaliphatic group can be unsubstituted or substituted with one or more substituents. Examples of substituents include, but are not limited to, various substituents such as, for example, halogens (—F, —Cl, —Br, and —I), additional aliphatic groups (e.g., alkenes, alkynes), aryl groups, alkoxides, carboxylates, carboxylic acids, ether groups, and the like, and combinations thereof. Examples of oxyaliphatic groups include, but are not limited to, oxyalkyl and oxy(aliphatic) hydroxy (e.g., oxy(alkyl)hydroxy). Additional examples of oxyaliphatic groups include, but are not limited to, oxyfluoroalkyl groups (e.g., oxytrifluoroethyl groups).

As used herein, unless otherwise indicated, the term "thioaliphatic" refers to branched or unbranched hydrocarbon groups comprising a sulfur atom and, optionally, one or more degrees of unsaturation. Degrees of unsaturation include, but are not limited to, alkenyl groups/moieties, alkynyl groups/moieties, and cyclic aliphatic groups/moieties. For example, the thioaliphatic group can be a $C_1$ to $C_{12}$, including all integer numbers of carbons and ranges of numbers of carbons there between, thioaliphatic group. The thioaliphatic group can be unsubstituted or substituted with one or more substituent. Examples of substituents include, but are not limited to, various substituents such as, for example, halogens (—F, —Cl, —Br, and —I), additional aliphatic groups (e.g., alkenyl groups and alkynyl groups), aryl groups, alkoxides, carboxylates, carboxylic acids, ether groups, and the like, and combinations thereof. Examples of thioaliphatic groups include, but are not limited to, thioalkyl, thioalkaryl, and thioaralkyl.

As used herein, unless otherwise indicated, the term "aryl" refers to $C_5$ to $C_{14}$, including all integer numbers of carbons and ranges of numbers of carbons therebetween, aromatic or partially aromatic carbocyclic groups. The aryl group can comprise polyaryl moieties such as, for example, fused rings or biaryl moieties. The aryl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof. Examples of aryl groups include, but are not limited to, phenyl groups, biaryl groups (e.g., biphenyl groups), and fused ring groups (e.g., naphthyl groups).

As used herein, unless otherwise indicated, the term "oxyaryl" refers to groups comprising the following structure:

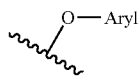

groups, where Aryl is as defined herein. Examples of oxyaryl groups include, but are not limited to, oxyphenyl groups and oxyphenylhydroxyl.

As used herein, unless otherwise indicated, the term "thioaryl" refers to groups comprising the following structure:

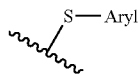

groups, where Aryl is as defined herein.

As used herein, unless otherwise indicated, the term "aminoaryl" refers to

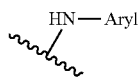

groups, where Aryl is as defined herein. The aminoaryl group can be substituted or unsubstituted with one or more substituent. Examples of substituents include, but are not limited to, various substituents such as, for example, aliphatic groups (e.g., alkenyl groups and alkynyl groups), aryl groups, alkoxides, carboxylates, carboxylic acids, ether groups, and the like, and combinations thereof.

As used herein, unless otherwise indicated, the term "arylamine" refers to groups comprising the following structures:

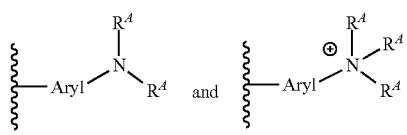

groups, where $R^A$ is hydrogen and where Aryl is as defined herein.

As used herein, unless otherwise indicated, the term "alkylarylamine" refers to groups comprising the following structures:

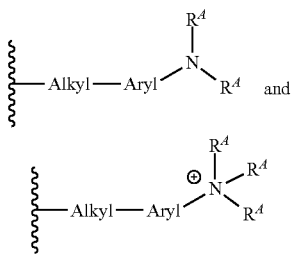

groups, where $R^A$ is hydrogen and where Alkyl and Aryl are as defined herein.

As used herein, unless otherwise indicated, the term "arylalkylamine" refers to groups comprising the following structures:

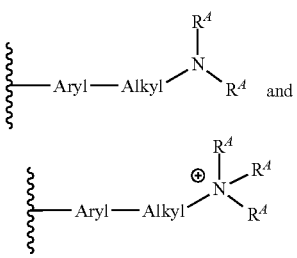

groups, where $R^A$ is hydrogen and where Alkyl and Aryl are as defined herein.

As used herein, unless otherwise indicated, the term "heteroaromatic" refers to a $C_5$ to $C_{14}$, including all integer numbers of carbons and ranges of numbers of carbons therebetween. monocyclic or bicyclic ring systems comprising one or two aromatic rings and containing at least one nitrogen, oxygen, or sulfur atom in an aromatic ring. The heteroaromatic groups can be substituted or unsubstituted. Examples of heteroaromatic groups include, but are not limited to, benzofuranyl, thienyl, furyl, pyridyl, pyrimidyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl groups.

As used herein, unless otherwise indicated, the term counterion is the ion that accompanies an ionic polyphosphazene or polyelectrolyte in order to maintain electric neutrality.

According to one aspect of the invention polyphosphazene macromolecules are provided, which may be used for treating cancer patients or other individuals in need of a stimulating immune response via activating TLRs. In embodiments, the disclosure provides for use of compositions described herein to achieve synergistic activation of multiple TLRs.

Polyphosphazenes are polymers with backbones consisting of alternating phosphorus and nitrogen atoms, separated by alternating single and double bonds. Each phosphorous atom is covalently bonded to two pendant groups ("R"). The repeat unit in polyphosphazenes has the following general formula:

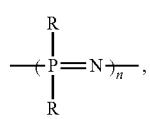

where n is an integer. For example, n is an integer from 10 to 500,000, including all integer values and ranges therebetween. Each R may be the same or different. Polyphosphazene may have a single substituent and said polyphosphazene is a homopolymer. Polyphosphazene may also have two or more types of pendant group and the groups vary randomly or regularly throughout the polymer. The phosphorus thus can be bound to two like groups, or to two different groups.

In a non-limiting embodiment, the polyphosphazene of the present invention is a polyphosphazene with ionic or ionizable side groups—polyphosphazene polyelectrolyte. Polyphosphazene polyelectrolytes useful in the present invention are, in a non-limiting embodiment, polyphosphazenes containing acidic or basic groups, and salt thereof. Examples of acidic groups include -phenylCO$_2$H, -phenylSO$_3$H, -phenylPO$_3$H, -(aliphatic)CO$_2$H, -(aliphatic)SO$_3$H, -(aliphatic)PO$_3$H, -phenyl(aliphatic)CO$_2$H, -phenyl(aliphatic)SO$_3$H, -phenyl(aliphatic)PO$_3$H, —[(CH$_2$)xO]yphenylCO$_2$H, —[(CH$_2$)xO]yphenylSO$_3$H, —[(CH$_2$)xO]yphenylPO$_3$H, —[(CH$_2$)xO]y(aliphatic)CO$_2$H, —[(CH$_2$)xO]y(aliphatic)SO$_3$H, —[(CH$_2$)xO]y(aliphatic)PO$_3$H, —[(CH$_2$)xO]yphenyl(aliphatic)CO$_2$H, —[(CH$_2$)xO]yphenyl(aliphatic)SO$_3$H, —[(CH$_2$)xO]yphenyl(aliphatic)PO$_3$H. Examples of basic groups include various aminogroups, such as -(aliphatic)N(CH$_3$)$_2$, -(aliphatic)N(C$_2$H$_5$)$_2$, -(aliphatic)NH$_2$, -(aliphatic)NH(CH$_3$), and alkylimidazoles. Polyphosphazene polyelectrolytes useful in the present invention can also include copolymers containing both acidic and basic groups, or polyampholytes, such as copolymers containing combinations of groups above or peptide side chains. The groups can be bonded to the phosphorous atom through, for example, an oxygen, sulfur, nitrogen, or carbon atom.

The polyphosphazenes of the present invention can be homopolymers, having one type of side groups, or mixed substituent copolymers, having two or more types of side groups. When polyphosphazene polymers of the present invention are copolymers and have two or more different types of side groups they can contain either different types of ionic groups or a combination of ionic and non-ionic groups. Side groups that do not contain ionic functionalities can be introduced in a polyphosphazene copolymer to modulate physical or physico-chemical properties of the polymer. Such side groups can be used, for example, to improve water solubility, to modulate biodegradability, to increase hydrophobicity, or to change chain flexibility of the polymer. These side groups (other than ionic groups as described above) may be one or more of a wide variety of substituent groups. As representative, non-limiting examples of such groups there may be mentioned: aliphatic; aryl; aralkyl; alkaryl; heteroaromatic; carbohydrates, including glucose, mannose; heteroalkyl; halogen; -oxyaryl including but not limited to -oxyphenyl, -oxyphenylhydroxyl; -oxyaliphatic including -oxyalkyl, and -oxy(aliphatic)hydroxyl, including oxy(alkyl)hydroxyl; -oxyalkaryl, -oxyaralkyl; -thioaryl; thioaliphatic including -thioalkyl; -thioalkaryl; thioaralkyl; aminoalkyl, aminoaryl, N-Ethylpyrrolidone, such as 2-(2-oxo-1-pyrrolidinyl)ethoxy; —NH—[(CH$_2$)x-O-]y-(aryl or aliphatic); and —O—[(CH$_2$)x-O-]y-(aryl or aliphatic); wherein x is 1-8 and y is an integer of 1 to 20.

In one non-limiting embodiment, the polyphosphazenes of the present invention are polyphosphazene polyacids, such as polyphosphazenes containing carboxylic acid side groups. In yet another non-limiting embodiment, the polymers of the present invention are homopolymers containing carboxylic acid side groups, such as poly[di(carboxylatophenoxy)phosphazene], or PCPP, and poly[di(carboxylatophenoxyethyl)phosphazene], or PCEP, and salts thereof, such as sodium or potassium salts, for example. In a preferred embodiment, the polymer of the present invention is a sodium salt of poly[di(carboxylatophenoxy)phosphazene]. In yet another embodiment, the polymer of the present invention is a potassium salt of poly[di(carboxylatophenoxyethyl)phosphazene].

In a non-limiting embodiment, the polyphosphazene polymer has an overall molecular weight of 5,000 g/mol to 10,000,000 g/mol, and in another embodiment from 40,000 g/mol to 1,000,000 g/mol.

The polyphosphazenes of the present invention, in a non-limiting embodiment, are polymers that may be biodegradable when administered to either humans or animals. Biodegradability of the polymer prevents eventual deposition and accumulation of polymer molecules at distant sites in the body, such as the spleen. The term biodegradable, as used herein, means a polymer that degrades within a period that is acceptable in the desired application, typically less than about five years and most preferably less than about one year.

The polyphosphazenes may be cross-linked ionically to form micro- or nanoparticles of various sizes to improve cellular uptake of the agent. Ionically cross-linkable polyphosphazenes, for example, can be cross-linked by treating a phosphazene polymer with a multivalent metal cation such as zinc, calcium, bismuth, barium, magnesium, aluminum, copper, cobalt, nickel, cadmium, or other multivalent metal cation known in the art; or with a multivalent organic cation such as spermine, spermidine, poly(ethyleneimine), poly (vinylamine), or other multivalent organic cation known in the art.

In a non-limiting embodiment, the polymers of the present invention may be prepared by producing initially a reactive macromolecular precursor such as, but not limited to, poly(dichlorophosphazene). The pendant groups then are substituted onto the polymer backbone by reaction between the reactive chlorine atoms on the backbone and the appropriate organic nucleophiles, such as, for example, alcohols, amines, or thiols. Polyphosphazenes with two or more types of pendant groups can be produced by reacting a macromolecular precursor, such as poly(dichlorophosphazene) with two or more types of nucleophiles in a desired ratio. Nucleophiles can be added to the reaction mixture simultaneously or in sequential order. The resulting ratio of pendant groups in the polyphosphazene will be determined by a number of factors, including the ratio of starting materials used to produce the polymer, the order of addition, the temperature at which the nucleophilic substitution reaction is carried out, and the solvent system used. While it is difficult to determine the exact substitution pattern of the groups in the resulting polymer, the ratio of groups in the polymer can be determined easily by one skilled in the art.

In a non-limiting embodiment, the polyphosphazene polyelectrolytes, such as one containing carboxylic acid groups can be produced as follows. An organic compound containing hydroxyl group and ester group may be reacted with reactive chlorine atoms on the polymer backbone. One or a mixture of organic compounds can be used to result in a homopolymer or a copolymer having more than one type of pendant group. Hydroxyl groups of the organic compound can be activated with sodium, sodium hydride, or sodium hydroxide by procedures known in the art and then reacted with chlorine atoms attached to the polyphosphazene backbone. After the completion of the reaction, the ester functionalities of the pendant groups may be hydrolyzed to yield carboxylic acid functionalities. All ester functionalities can be hydrolyzed to achieve full conversion into the acid groups, or, if desired, the reaction can be stopped before completion, thereby resulting in a substituted copolymer containing both acid and ester functionalities. The polymer then can be dissolved in an aqueous solution at a desired concentration. The acid groups also can be converted into salt form, such as sodium or potassium, if required to improve solubility or to achieve desired polymer conformation and physico-chemical characteristics.

Polyphosphazene poly-TLR agonists may be formulated with (a composition may comprise) vaccine antigens to create an anticancer vaccine. The antigen can be a protein, peptide, polysaccharide, glycoprotein, glycolipid, or combination thereof, which elicits an immunogenic response in a human; or in an animal, for example, a mammal, bird, or fish. The vaccine antigens of the invention may be a cancer or tumor antigen including but not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER2 antigen, polymorphic epithelial mucin (PEM), malignant human lymphocyte antigen-APO-1, differentiation antigen such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, D.sub.156-22 found in colorectal cancer, TRA-1-85 (blood group H), C14 found in colonic adenocarcinoma, F3 found in lung adenocarcinoma, AH6 found in gastric cancer, Y hapten, Le.sup.y found in embryonal carcinoma cells, TL5 (blood group A), EGF receptor found in A431 cells, E.sub.1 series (blood group B) found in pancreatic cancer, FC 10.2 found in embryonal carcinoma cells, gastric adenocarcinoma antigen, CO-514 (blood group Lea) found in Adenocarcinoma, NS-10 found in adenocarcinomas, G49 found in EGF receptor of A431 cells, MH2 found in colonic adenocarcinoma, CA-19.9 found in colon cancer, gastric cancer mucins, TA7 found in myeloid cells, R24 found in melanoma, 4.2, $G_D3$, D1.1, OFA-1, $G_M2$, OFA-2, $G_D2$, and M1:22:25:8 found in embryonal carcinoma cells, and SSEA-3 and SSEA-4 found in 4 to 8-cell stage embryos, and T cell receptor derived peptide from a Cutaneous T cell Lymphoma.

In a non-limiting embodiment, the polyphosphazene of the present invention may be formulated with (a composition may comprise) other immunomodulating compounds or TLR agonists. Typical examples of such immunomodulating compounds include, but are not limited to poly- or oligo-nucleotides (DNA sequences), such as CpG (TLR9 agonist), imidazoquinolines, such as R848, or thiazoloquinolines, such as CL075, or guanosines, such as Loxoribine (TLR 7/8 agonists), polyadenylic-polyuridylic and polyinosine-polycytidylic acids (TLR3 agonists), derivatives of lipopolysaccharides, such as monophosphorlyl lipid (MPL), muramyl dipeptide (MDP) and threonyl muramyl dipeptide (tMDP).

In yet another non-limiting embodiment, the polyphosphazene of the present invention may be formulated with (a composition may comprise) anticancer drugs, such as cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, folinic acid, and oxaliplatin.

The formulation (composition) of polyphosphazene of the present invention also may include one or more pharmaceutically acceptable and/or approved additives (excipients), antibiotics, preservatives, diluents and stabilizers. Such substances include, but are not limited to, water, saline, glycerol, ethanol, wetting or emulsifying compounds, pH buffering substances, stabilizing compounds such as polyols, for example trehalose, or the like.

In a non-limiting embodiment, the at least one polyphosphazene agent may be formulated or encapsulated in various forms or encapsulation media, such as in microspheres, nanospheres, microcapsules, nanocapsules, microgels, nanogels, liposomes, or dendrimers. The above-mentioned forms may modulate the release profile in order to achieve a desirable biological (therapeutic) effect. For example, such forms may provide a controlled release of at least one polyphosphazene agent over a desired period of time.

The formulation (composition) of polyphosphazenes of the present invention can comprise any liquid or solid that is compatible with the polyphosphazene of the present invention. It can be a solution or a dispersion, such as an emulsion or suspension. It can be water based or can contain organic solvents, or a mixture of water and organic solvents. In one embodiment, the formulation is water or an aqueous based formulation. It can contain salts, acids, bases, or other excipients to maintained a desired pH and ionic strength. The formulation can be also a solid coating deposited on microneedles for intradermal delivery or the entire material microneedles are made of.

The polyphosphazene of the present invention is used in an amount effective to provide the desired immune response. The immunotherapy can be administered by any method known to those skilled in the art that elicits an immune response; including parenteral, transcutaneous, oral, or transmucosal administration. In embodiments, a composition of this disclosure is used as or in combination with a vaccine.

Compositions of the disclosure can be administered parenterally (intravenously, intramuscularly, subcutaneously) or transcutaneously (intradermally), or orally to an individual in need thereof.

In embodiments, the disclosure comprises administering a composition of this disclosure to an individual, thereby activating TLRs in the individual. In a non-limiting embodiment, polyphosphazenes and compositions of this disclosure can activate TLR7, TLR8, and TLR9 of the immune system of a mammal. In yet another embodiment, polyphosphazenes and compositions of this disclosure can activate TLR7, TLR8, TLR9, and TLR3 of the immune system of a mammal. "Activation" and "activating" a TLR as used herein means promoting TLR signaling. In embodiments, activation of one or more TLRs stimulates an innate immune response. In an embodiment, TLR signaling promoted using compositions of this disclosure proceeds through a MyD88-dependent pathway, and as a result, inflammatory cytokines are produced by cells that express one or more of the activated TLRs. In another and not necessarily mutually exclusive embodiment, TLR signalling promoted using compositions described herein proceeds through MyD88-independent pathway, which is known to be associated with production IFN-β, and maturation of dendritic cells.

In certain embodiments, the disclosure comprises use of a composition of this disclosure to activate distinct TLRs on one or more cell types. In embodiments, the cell types comprise one or a combination of monocytes, macrophages, dendritic cells, Mast cells, B cells, T cells, or cells of the intestinal epithelium. Any parameter described herein can be compared to any suitable reference. In examples, a suitable reference comprises a value obtained or derived from one or more control experiments, or may comprise a known value or range of values, a statistical value, such as an area under a curve, etc. In examples, activation of one or more TLRs as described herein is compared to a control, and wherein a composition of the disclosure elicits a TLR-mediated response that is greater than a control, and wherein the response may be a synergistic response. In an embodiment, the disclosure comprises using a composition of this disclosure to produce syngergistic production of a tumor necrosis factor alpha (TNF-α). In embodiments, TNF-α production produced by PCPP+R848 is more than additive relative to the combined production of TNF-α promoted by PCPP and R848 when each of these agents is used in the absence of the other. In embodiments, the disclosure provides for stimulating increased interleukins (IL), such as IL-6 and IL-12, relative to a control.

The disclosure encompasses effects of compounds of this disclosure on T-cells. In embodiments, we demonstrate that polyphosphazene formulations have the ability to induce a Th1-biased response in the absence of a strong immunopotentiator, such as a known TLR agonist (as shown in Cayatte, et al. *Mol. Pharmaceutics*, 2017, 14 (7), pp 2285-2293, from which the description of PCPP-containing compounds and use of them is incorporated herein by reference). This was evidenced by a ratio of IFN-γ/IL-5 production and low levels for IL-13 present in lungs post-respiratory syncytial virus (RSV) challenge in an animal model. Further, we have demonstrated that, in contrast to the PCPP-R848 system of the present disclosure, addition of PCPP to another TLR agonist (CpG) did not induce higher cytokine levels compared to CpG alone. This shows the absence of synergistic effects on cytokine production in the PCPP-CpG formulation, thus rendering the PCPP+R848 results demonstrated herein unexpected. Further, we demonstrated that PCPP displays high immunoadjuvant potency when formulated with RSV sF antigen. PCPP formulations induce high neutralization titers similar to alum formulations. While alum protected animals against challenge in the lung, PCPP formulation provided complete protection against challenge both in the lung and in the upper respiratory tract. Thus, the disclosure is suitable for use in a variety of settings wherein stimulation of an immune response is desirable.

In embodiments, compositions of this disclosure can further comprise an antigen, or can be administered sequentially with an antigen, and thus the compositions can function as a vaccine and/or vaccine adjuvant. In embodiments, It is contemplated that the present invention can be used to stimulate an immune response to any antigen. The antigens include but are not limited to protein, polypeptide or peptide antigens. The antigen may be well characterized, or may be unknown, other than by a known presence in, for example, a lysate from a particular cell type.

In embodiments, compositions of this disclosure are used with an antigen to facilitate an enhanced immune response against a tumor antigen. Tumor antigens can be obtained by conventional techniques, such as by preparation of tumor cell lysates by repeatedly freezing and thawing tumor cells/tissues obtained from either fresh tumor biopsy tissues or from tumor cells generated in vitro by tissue culture. The tumor lysate can be obtained by centrifugation and harvesting the supernatant fluid. The tumor cell lysates can be used immediately or frozen and stored until ready for use. The antigen can be used in a purified form or in partially purified or unpurified form as cell lysate. Thus, in embodiments, a tumor or portion thereof from an individual may be used to obtain an antigen and compositions of this disclosure can be used to promote and/or improve an immune response to the antigen.

In various embodiments, the antigen may be an antigen expressed by any type of cancer cell, specific examples of which include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia, and heavy chain disease.

In other embodiments, the antigens used in the invention may be those expressed by infections agents. Examples of such infectious agents include, but are not limited to viruses, bacteria, fungi and other parasites. Examples of viruses include, but are not limited to, hepatitis type B or type C, influenza, vaticella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I or type II. Examples of bacteria include, but are not limited to, *M. tuberculosis*, mycobacterium, mycoplasma, *Neisseria* and *Legionella*. Examples of other parasites include, but are not limited to, rickettsia and chlamydia.

Administration of the compositions of the invention can be performed in conjunction with conventional therapies that are intended to treat a disease or disorder associated with the antigen. For example, the composition could be administered prior to, concurrently, or subsequent to conventional anti-cancer therapies. Such therapies can include but are not limited to chemotherapies, surgical interventions, and radiation therapy.

In general, an appropriate dosage and treatment regimen provides the composition in an amount effective to stimulate an immune response that provides a therapeutic and/or prophylactic benefit. Such a response can be monitored by an improved clinical outcome, e.g., inhibition in tumor growth and/or metastasis, improved resistance to infection, improved immune cell activation, and/or other parameters that will be apparent to those skilled in the art, dependant upon the condition being treated.

Routes and frequency of administration of the therapeutic compositions disclosed herein, as well as dosage, will vary from individual to individual, and may be readily established using standard techniques.

The invention is further illustrated by the following non-limiting examples.

Example 1. Interactions Between Polyphosphazenes and TLRs in Solution

Figure 2:
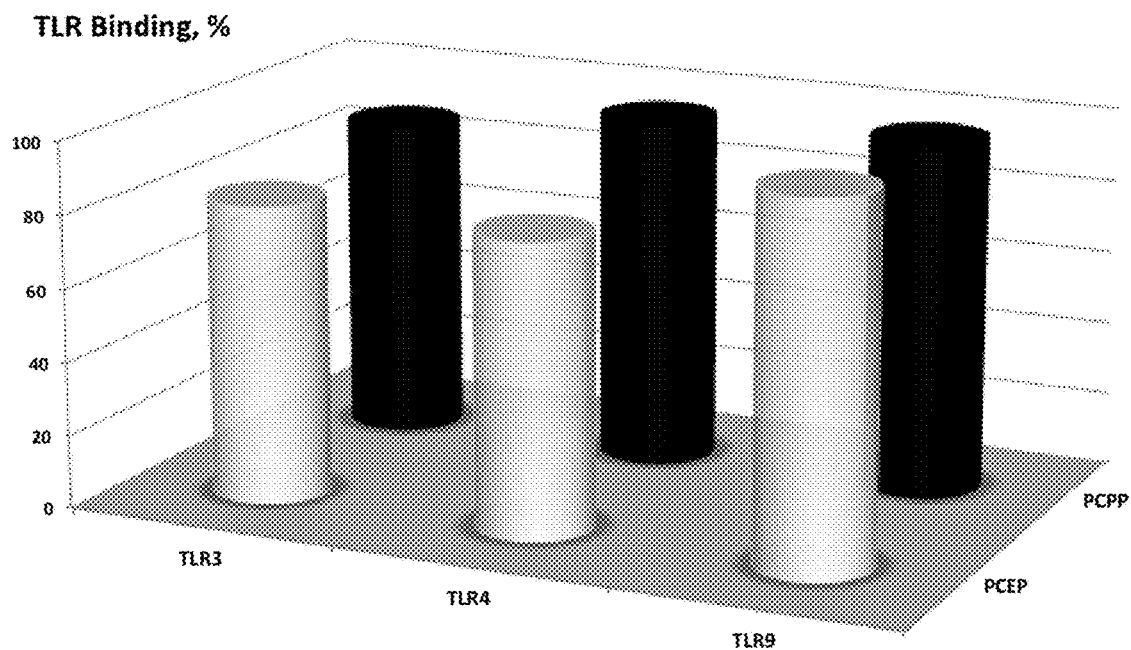
FIG. 2 illustrates binding of soluble TLRs with PCPP (black) or PCEP (grey) as determined by field flow fractionation (AF4) (1 mg/mL PCPP or PCEP, 0.05 mg/mL protein, PBS, pH 7.4). Asymmetrical Flow Field Flow Fractionation (AF4) is an analytical method allowing separation of complex molecular or particular mixtures by their size. Formulations are dissolved in the mobile phase (PBS, pH 7.4) and separated in a channel containing semi-permeable membrane, to which an external cross-flow of the same mobile phase is applied, which acts perpendicular to the carrier-flow resulting in sample separation. The size-dependent diffusion abilities of molecules lead to an arrangement in different layers of the parabolic flow profile inside the channel with small molecules eluting first and the larger molecules or particles eluting later.

PCPP and PCEP were investigated for their interactions with soluble TLR3, TLR4, and TLR9 using asymmetrical flow field flow fractionation method (AF4) in solution under physiological conditions. Formulations were dissolved in PBS (pH 7.4) and separated in a channel, to which an external cross-flow, which acted perpendicular to the carrier-flow resulting in sample separation. The size-dependent diffusion abilities of molecules lead to an arrangement in different layers of the parabolic flow profile inside the channel with small molecules eluting first and the larger molecules or particles eluting later. The extent of binding was evaluated by the decrease of a TLR protein peak in its formulation with polyphosphazene compared to the same peak in the absence of polymer and presented as a percent of total protein in the experiment. The results are shown in FIG. 2. As seen from the Figure, both polyphosphazenes demonstrate strong interactions with soluble receptors under physiological conditions. These results indicate a possibility of activation of dendritic by PCPP and PCEP through TLR signaling pathway, both on cell surface (TLR4) and endosomal (TLR3 and −9) levels.

Example 2. Activation of TLR Signaling Pathways by Polyphosphazenes in Cellular Assays PCPP and PCEP were screened for their ability to stimulate TLR signaling in cells. The assay utilized HEK293 derived cells overexpressing a given human TLR gene. Monitoring of signaling through the TLR is based on the activation of a transcription factor -nuclear factor-kappa B (NF-kB). The secreted embryonic alkaline phosphatase (SEAP) reporter is used, which is under the control of a promoter inducible by the transcription factor NF-κB. In a 96-well plate (200 μL total volume) containing the appropriate cells (50,000-75,000 cells/well), 20 μL of the polymer solution or the positive control ligand was added to the wells. The media added to the wells is designed for the detection of NF-κB induced SEAP expression. After a 16-24 hr incubation the optical density (OD) was read at 650 nm on a Molecular Devices SpectraMax 340PC absorbance detector. All experiments were performed in triplicates. The following control ligands were used: hTLR2: HKLM (heat-killed *Listeria monocytogenes*) at 1×108 cells/mL, hTLR3: Poly(I:C) HMW at 1 g/mL, hTLR4: *E. coli* K12 LPS at 100 ng/mL, hTLR5: *S. typhimurium* flagellin at 100 ng/mL, hTLR7: CL307 at 1 μg/mL, hTLR8: CL075 at 1 μg/mL, hTLR9: CpG ODN2006 at 100 ng/mL. Negative Control Cell Lines (TLR−) were as follows: HEK293/Null1: TNFα at 100 ng/mL (control for human TLR2, 3, 5, 8 and 9), HEK293/Null1-k: TNFα at 100 ng/mL (control for humanTLR7), HEK293/Null2: TNFα at 100 ng/mL (control for human TLR4).

Figure 3:
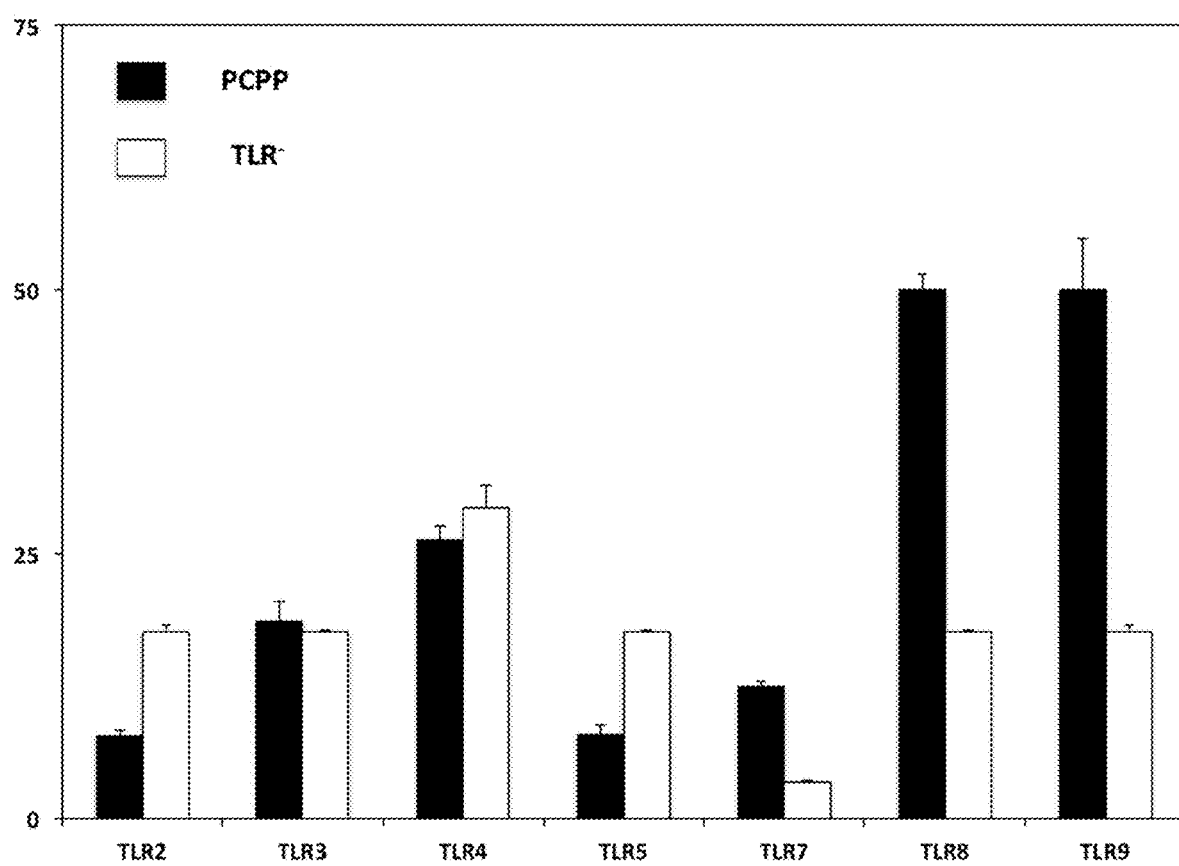
FIG. 3 illustrates TLR stimulation by PCPP as assessed by NF-kB activation in HEK293 cells, which utilize secreted embryonic alkaline phosphatase (SEAP) reporter gene as a read-out. Cell stimulation was measured as a 'Fold Induction' factor—the ratio of optical densities (alkaline phosphatase activities) measured in the presence and absence of the polymer. The 'Fold Induction' factor for each polymer is then expressed in a graph as a percent of the same factor for the positive control. Black bars represent values for cells expressing given TLRs for PCPP. Empty bars show data for the same polymers and cell lines, which do not express any TLR, but still have an NF-kB inducible reporter (TLR⁻ negative control cell lines). The values on the graph represent averages of three screenings and expressed in percent of cells activated by a positive control.
Figure 4:
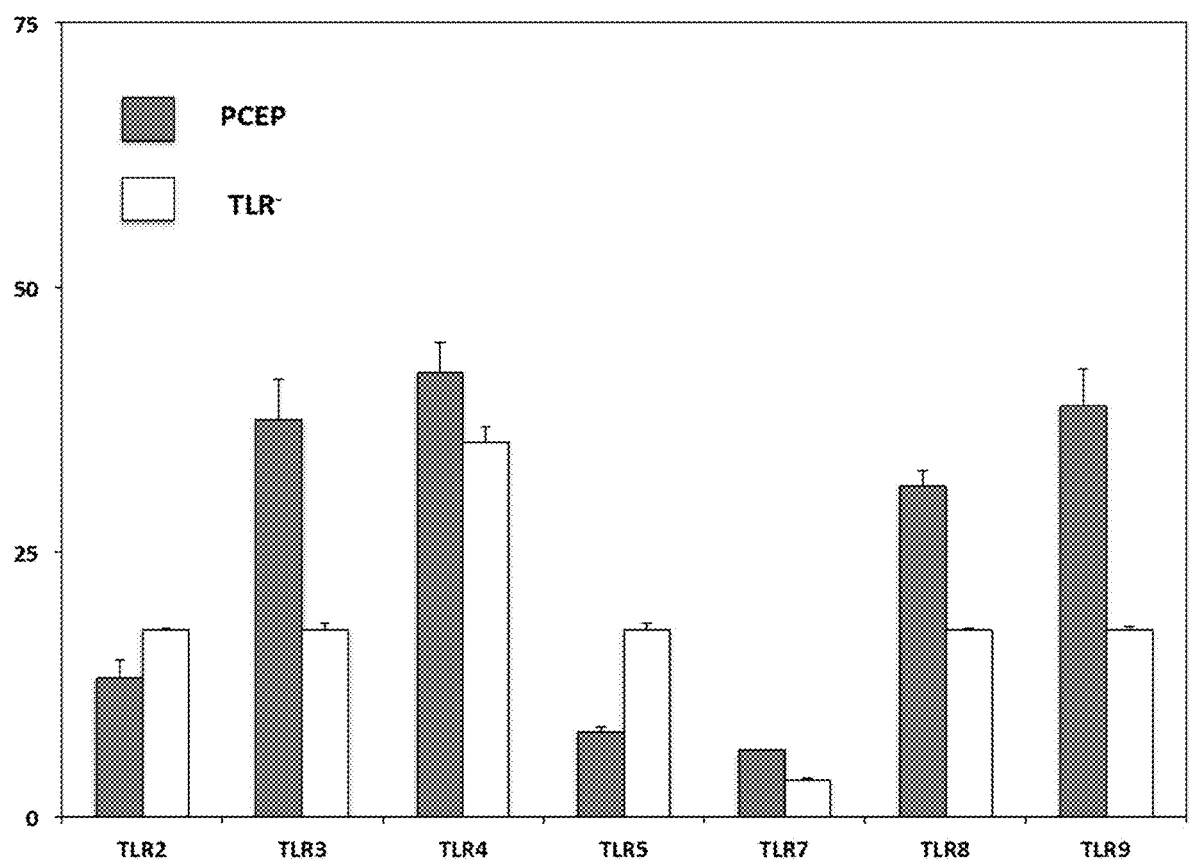
FIG. 4 illustrates TLR stimulation by PCEP as assessed by NF-kB activation in HEK293 cells, which utilize secreted embryonic alkaline phosphatase (SEAP) reporter gene as a read-out. Cell stimulation was measured as a 'Fold Induction' factor—the ratio of optical densities (alkaline phosphatase activities) measured in the presence and absence of the polymer. The 'Fold Induction' factor for each polymer is then expressed in a graph as a percent of the same factor for the positive control. Grey bars represent values for cells expressing given TLRs for PCEP. Empty bars show data for the same polymers and cell lines, which do not express any TLR, but still have an NF-kB inducible reporter (TLR-negative control cell lines). The values on the graph represent averages of three screenings and expressed in percent of cells activated by a positive control.

The results of these studies are shown in FIG. 3 for PCPP and FIG. 4 for PCEP. In these Figures cellular responses are presented as a percent of the positive control, which is individual for each given TLR. Empty bars show data for the same polymers and the cell lines, which do not express any TLR, but still have an NF-kB inducible reporter (TLR-negative control cell lines). Both PCPP and PCEP were able to stimulate cellular responses in these assays. However, the strongest responses for TLR overexpressed cells with minimal TLR-stimulation are observed for TLR7, TLR8 and TLR9 for PCPP and the same receptors, plus TLR 3 for PCEP.

Example 3. Water-Soluble Imidazoquinoline Multimers

Imidazoquinoline compounds, such as Imiquimod and Resiquimod (R-848), are shown to be topically active immune response modifiers and possess both anti-viral and anti-tumor properties [Hemmi, H., et al. Nat Immunol 2002, 3, (2), 196-200]. These low molecular weight synthetic molecule activate immune cells via the Toll-like receptor TLR7/TLR8-dependent signaling pathway [Hemmi, H., et al. Nat Immunol 2002, 3, (2), 196-200]. Resiquimod has also demonstrated a strong potency as vaccine adjuvant enabling Th1 biased immune responses [Weeratna, R. D., et al. Vaccine 2005, 23, (45), 5263-5270; Tomai, M. A., et al. Expert Review of Vaccines 2007, 6, (5), 835-847. Because of the hydrophobic nature of imidazoquinolines, they are traditionally not administered systemically and have to be formulated in liposomes [Peine, K. J., et al., Liposomal resiquimod for the treatment of *Leishmania donovani* infection. Journal of Antimicrobial Chemotherapy 2013, dkt320], in polymer microparticles [Duong, A. D., et al. Molecular Pharmaceutics 2013, 10, (3), 1045-1055; Thomsen, L. L., et al. Vaccine 2004, 22, (13), 1799-1809], adsorbed on Alum [Zhou, C.-X, et al., BMC Veterinary Research 2014, 10, 2], or dissolved in buffers containing DMSO [Weeratna, R. D., et al.]. This Example addresses the need for a water-soluble formulation of imidazoquinoline compounds. Accordingly, the disclosure encompasses novel macromolecular compounds of the following formula, which are based on water-soluble polyphosphazene polyacids containing imidazoquinolines as counterions:

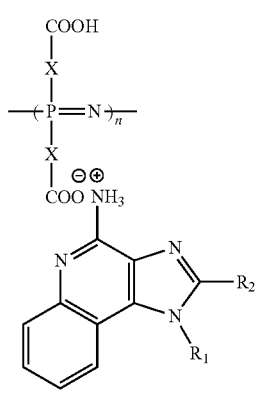

wherein R₁ selected from the following groups:

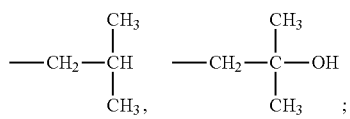

R₂ selected from the following groups: —H, —CH₃ or —CH₂—CH₂—CH₃,

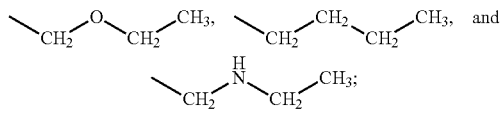

X is selected from the following oxyaryl and oxyalkaaryl linking moieties, which link an anionic group (e.g., —C(O)O⁻) to the polyphosphazene backbone via covalent bonds):

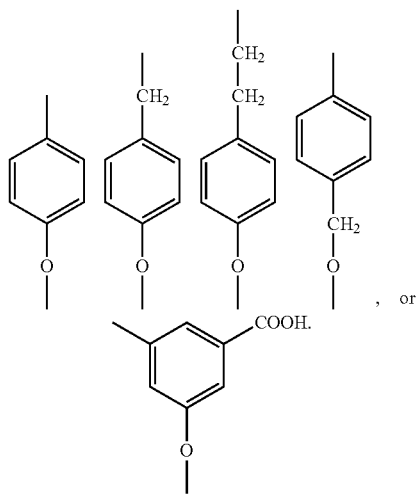

Although imidazoquinolines are usually not charged at near physiological pH and are not expected to bind negatively charged polyphosphazene polyacids, we found that mixing these components at slightly acidic conditions or their co-precipitation result in macromolecular compounds, which maintain their composition at neutral conditions.

Specifically, the solution of resiquimod (R-848, S-28463 or 1-[4-amino-2-(ethoxymethyl) imidazo[4,5-c]quinolin-1-yl]-2-methylpropan-2-ol) chloride in deionized water was added to aqueous solution of poly[di(carboxylatophenoxy)phosphazene], sodium salt (PCPP) and then the pH was adjusted to pH 7.4. The macromolecular compound (PCPP-R848) of the following formula was obtained:

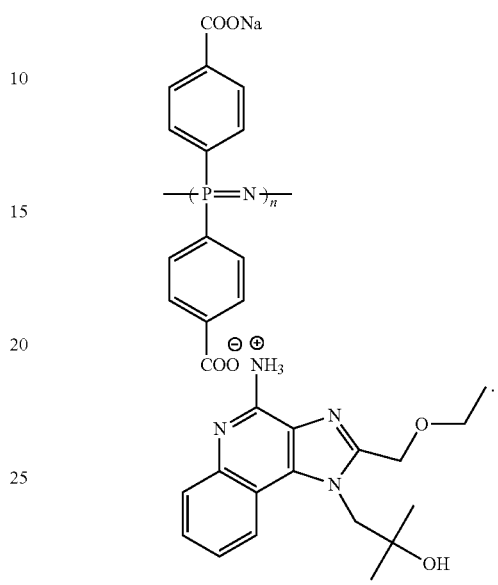

Figure 5:
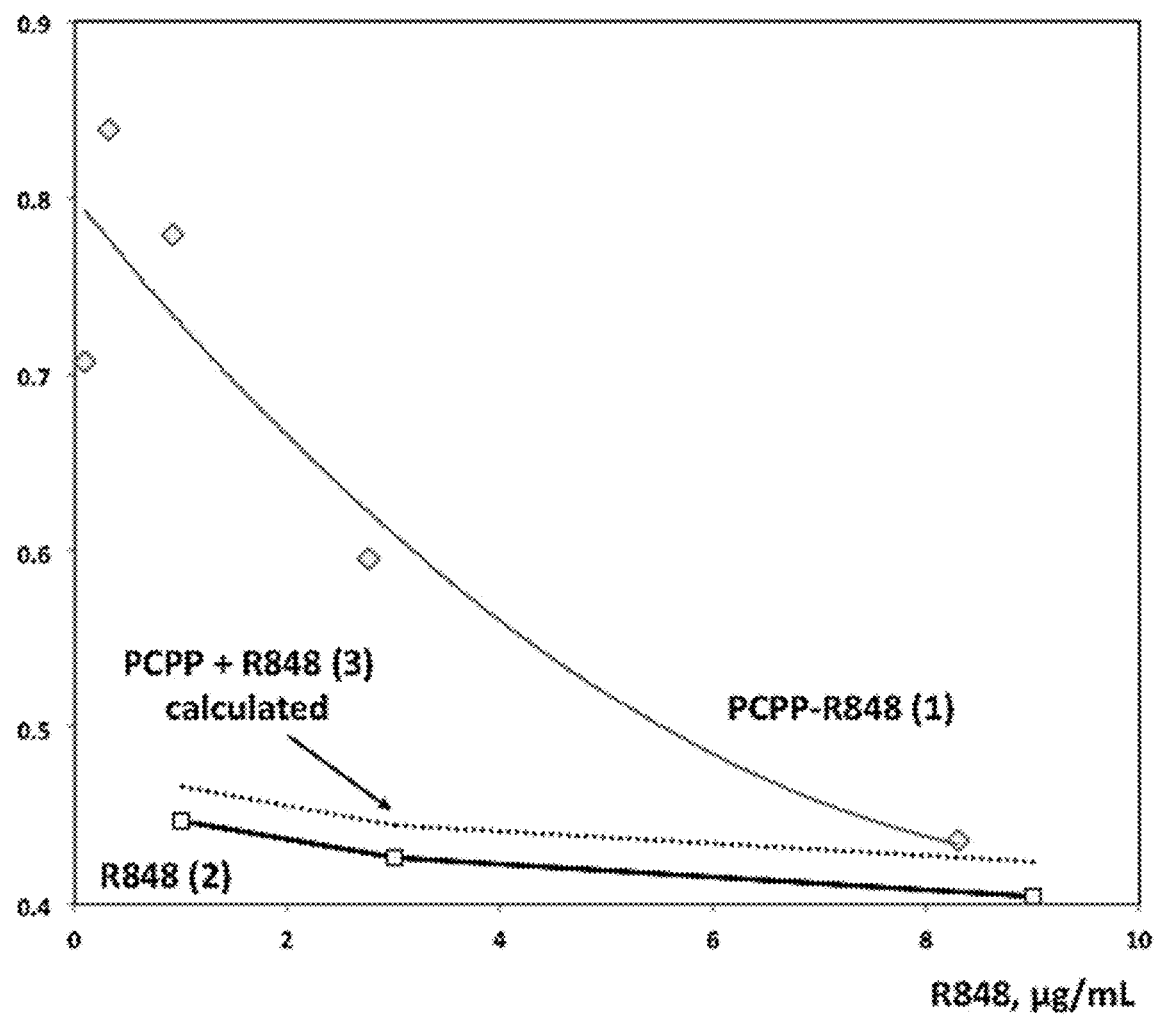
FIG. 5 illustrates induction of TNFα by PCPP-R848 compound at 2:1 ratio w/w (1), R-848 (2) and calculated sum of cytokine levels induced by R-848 and PCPP separately (3) versus concentration of R848.

The antitumor activity of this compound was evaluated in cellular assays using mouse splenocytes by measuring the release of Tumor Necrosis Factor (TNFα). The activity of PCPP-R848 was compared to those of PCPP and R848 alone. FIG. 5 shows the induction of TNFα by PCPP-R848 compound at 2:1 ratio w/w (1), R-848 (2) and calculated sum of cytokine levels induced by R-848 and PCPP separately (3) versus concentration of R848. Unexpectedly, the compound of present invention (PCPP-R848) shows TNFα induction, which is almost two fold higher than the sum of those effects induced by the components separately.

Preparation of PCPP-R848

PCPP-R848 multimers were produced by (1) preparing a soluble salt form of R848 at acidic conditions (pH 6.0-6.2), (2) preparing a soluble PCPP at neutral conditions (pH 7.0-7.4), and (3) adding solution of R848 to a solution of PCPP to form an insoluble precipitate, which then is dissolved in solutions at neutral pH. Alternatively, PCPP-R848 multimers may be formed by adding a solution of R848 to a large excess of dilute PCPP solution upon stirring, so that neither component precipitates.

Example 4. Preparation of PCPP-R848 by Precipitation 10 mg of R848 was dissolved with 1.97 mL deionized water without stirring, then 0.03 mL of 1 N hydrochloric acid was added to the mixture and vortexed until complete dissolution (3-5 minutes, pH 4). 0.0028 mL 1 N sodium hydroxide was added to the solution to adjust pH to 6.0-6.7. The solution was filtered using 0.22 μm Millex®-GV filter.

Figure 6:
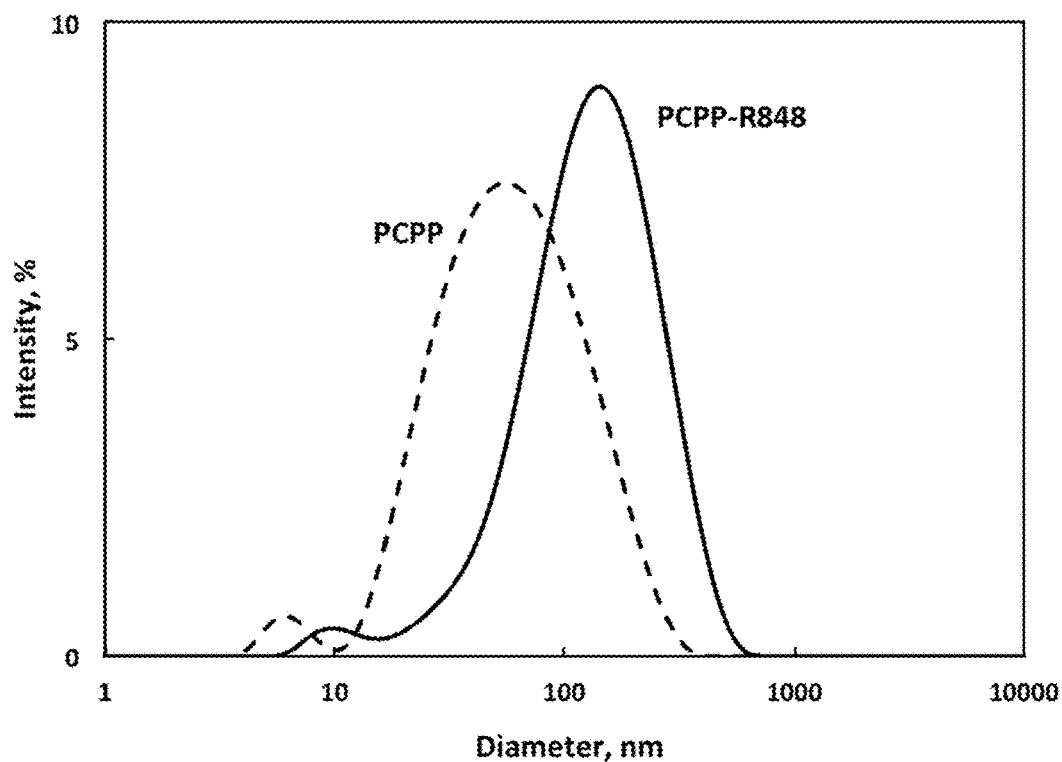
FIG. 6 illustrates Dynamic Light Scattering (DLS) profiles displaying molecular seize distribution of PCPP and PCPP-R848 complex (produced as in Example 4).
Figure 7:
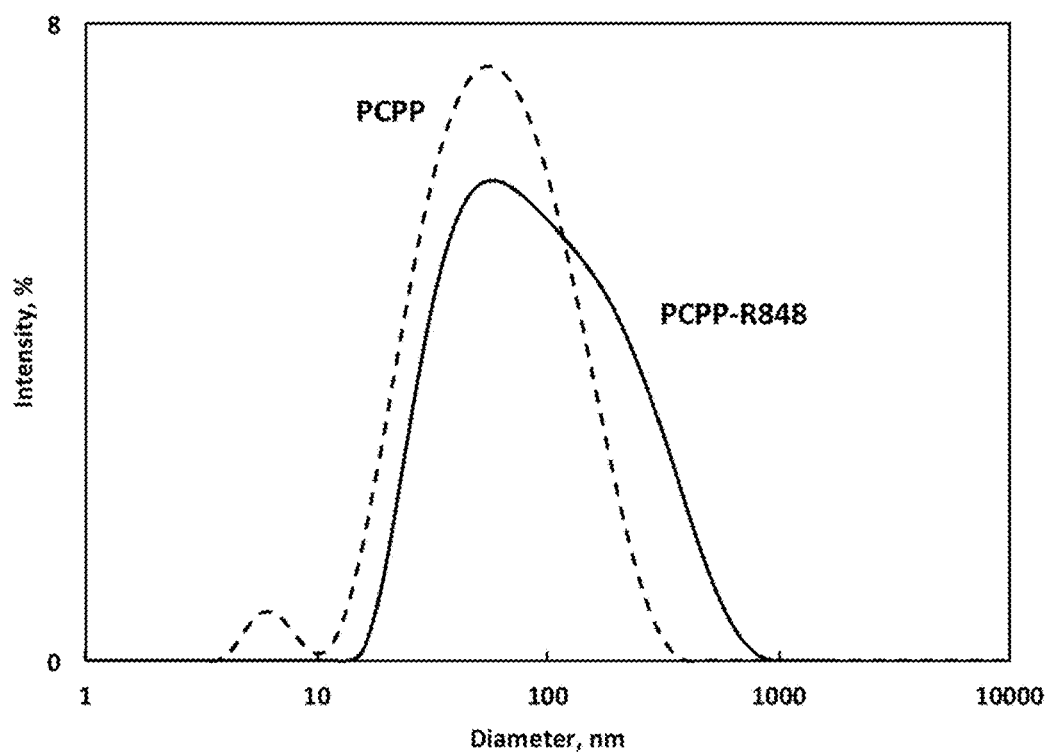
FIG. 7 illustrates DLS profiles of PCPP and PCPP-R848 complex (produced as in Example 5).

0.25 mL of 2 mg/mL PCPP (1.6 μmol carboxyl groups) in PBS was mixed with 0.25 mL PBS (pH 7.4), to which 0.5 mL of 5 mg/mL (1.6 μmol) R848 solution was added and vortexed for 2 min. The mixture was centrifuged at 14000 rpm for 10 minutes, supernatant was removed and the precipitate was resolved in 1 ml of PBS. FIG. 6 shows dynamic light scattering profiles of PCPP and PCPP-R848 formulation, which demonstrate the formation of the PCPP-R848 complex with larger molecular dimensions than PCPP.

Example 5. Preparation of PCPP-R848 in Solution

Solution of R848 was prepared as described in Example 4. 0.1 mL of 2 mg/mL PCPP (0.6 µmol carboxyl groups) in PBS was mixed with 0.8 mL PBS (pH 7.4), then 0.1 mL of 5 mg/mL of R848 (0.3 µmol) was added to the solution and vortexed for 2 min.

Example 6. Immunostimulatory Activity of PCPP and PCPP-R848 Formulations

Figure 8:
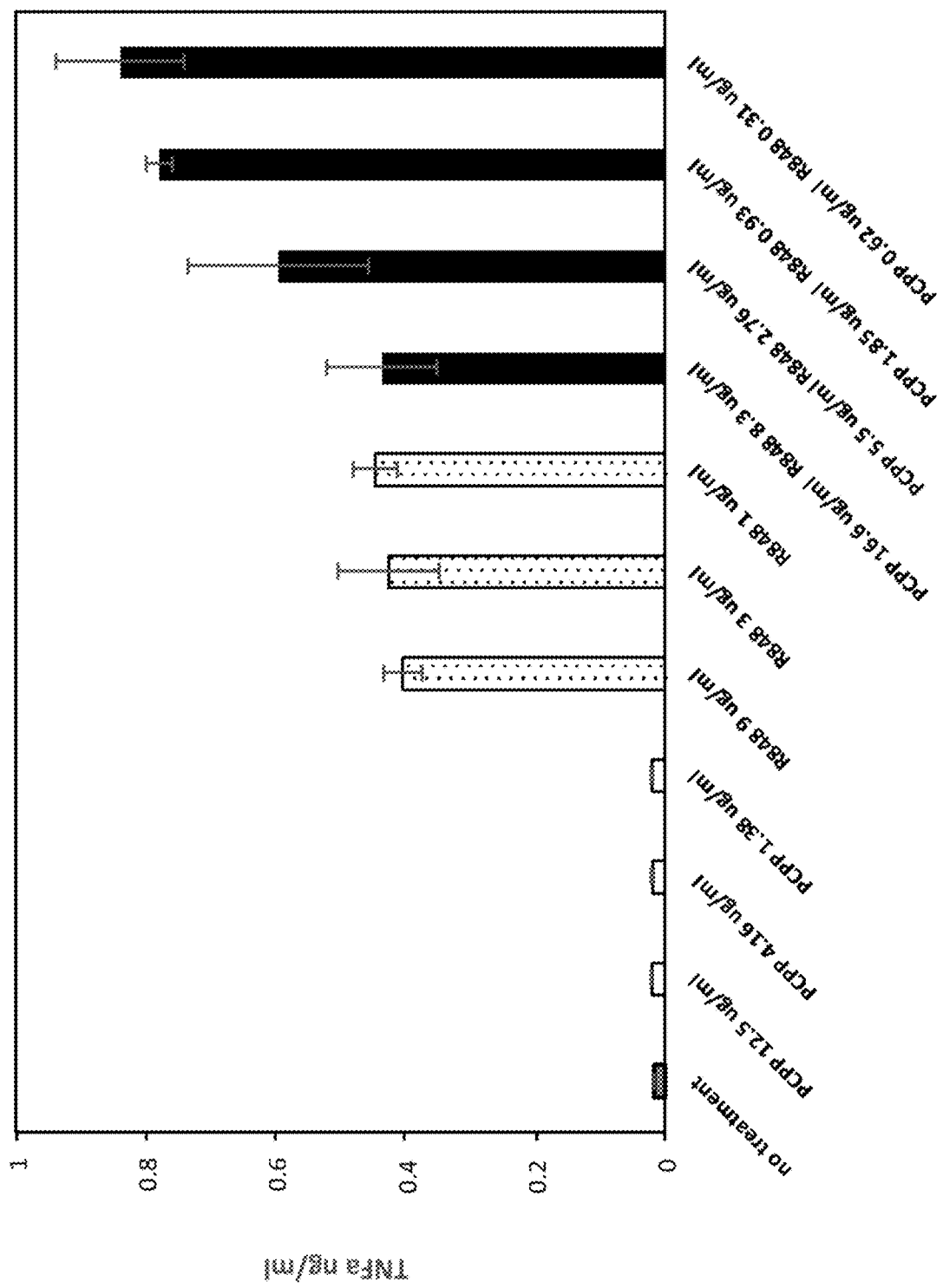
FIG. 8 illustrates induction of TNFα by PCPP, R848, and PCPP-R848 formulations in mouse splenocytes (48 hour incubation).
Figure 9:
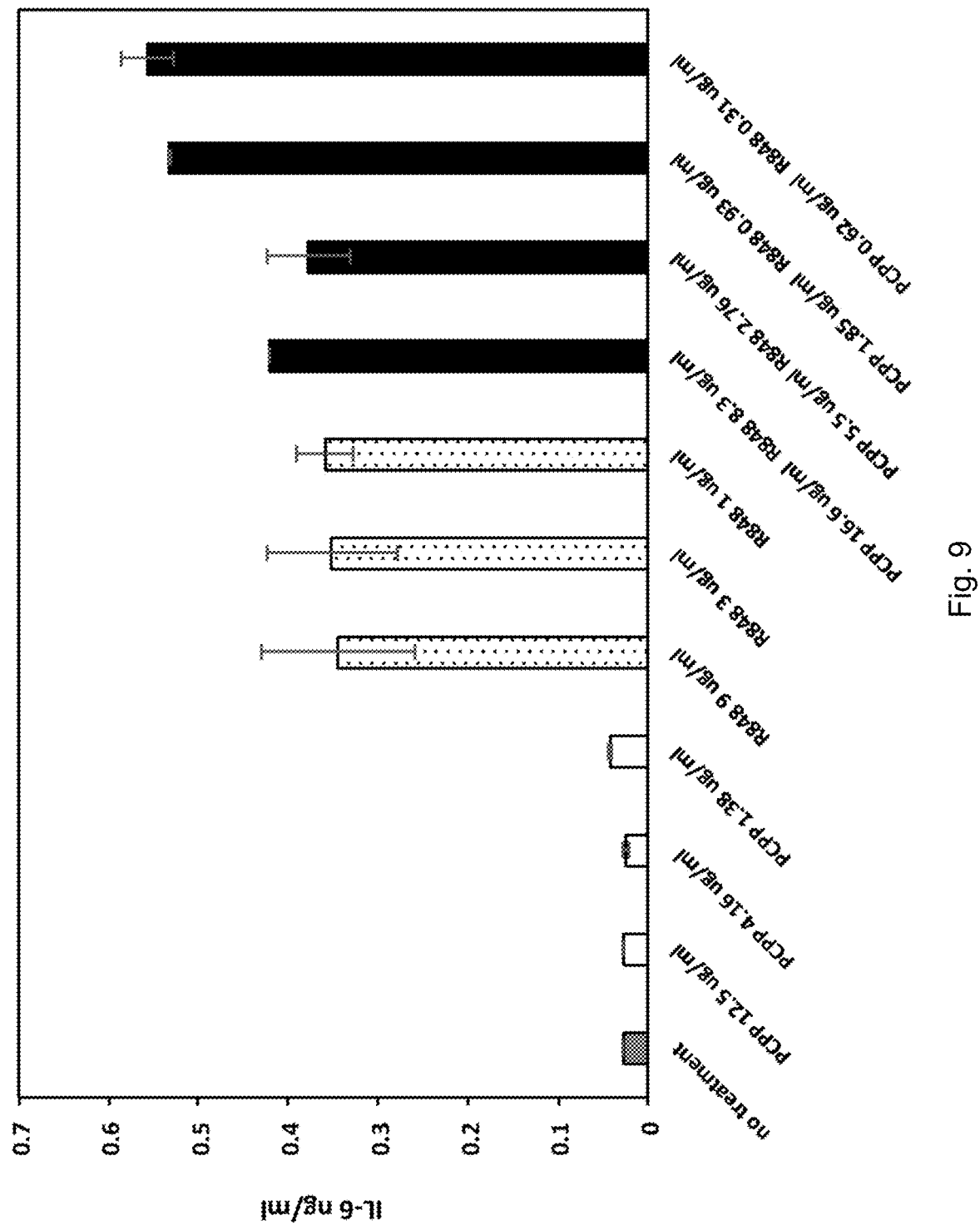
FIG. 9 illustrates induction of IL-6 by PCPP, R848, and PCPP-R848 formulations in mouse splenocytes (48 hour incubation).
Figure 10:
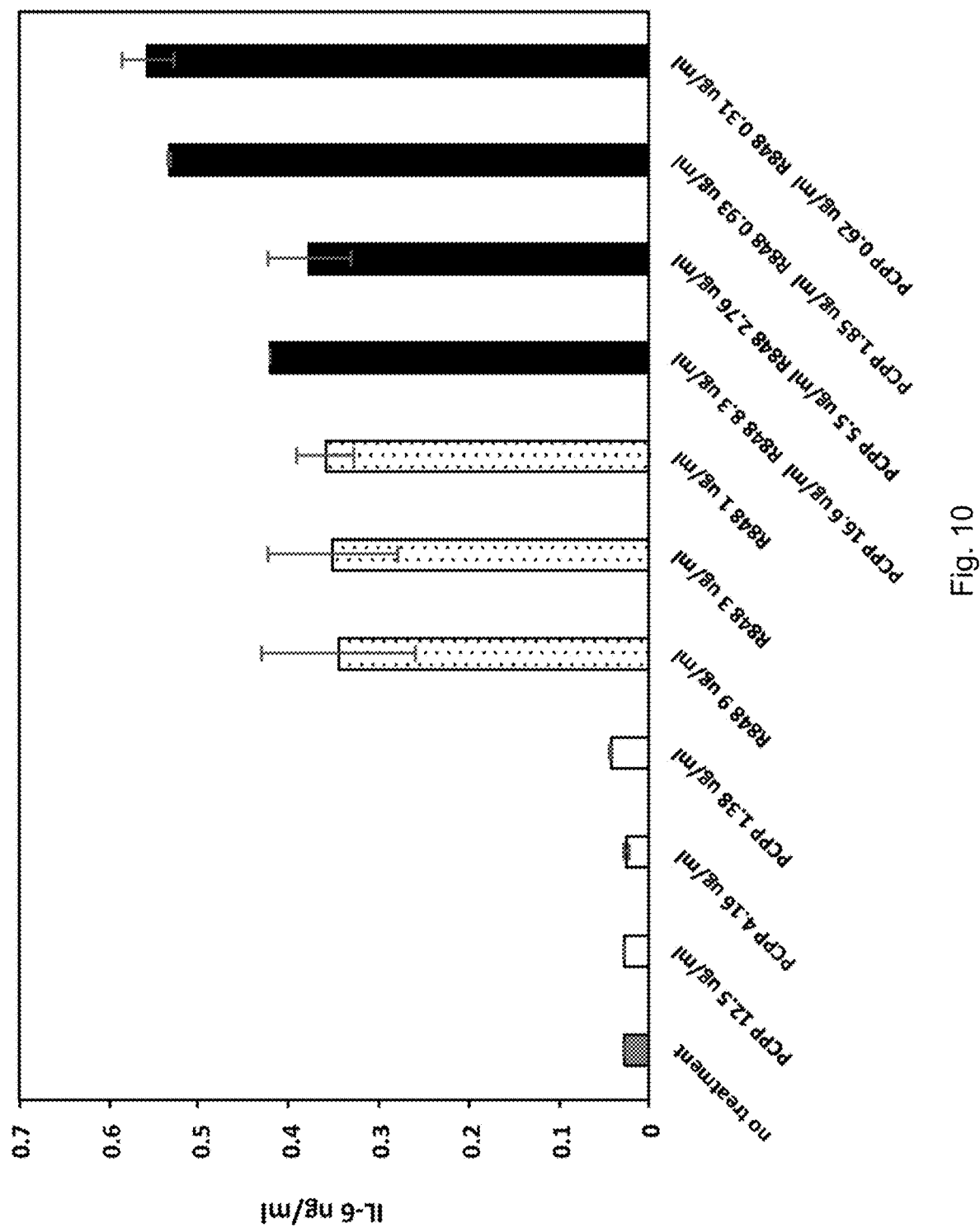
FIG. 10 illustrates induction of IL-12 by PCPP, R848, and PCPP-R848 formulations in mouse splenocytes (48 hour incubation).

Immunostimulatory activity of PCPP and PCPP-R848 formulations was evaluated in cellular assays using mouse splenocytes by measuring the release of Tumor Necrosis Factor (TNFα), Interleukin 6 (IL-6), and Interleukin 12 (IL-12). The results are shown in FIGS. 8-10. As seen from figures, PCPP-R848 formulations displayed higher immunostimulatory activity for all cytokines compared to PCPP and R848 separately. Unexpectedly, the levels of released cytokines observed for PCPP-R848 are higher than added levels for individual components (PCPP and R848).

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A polyphosphazene having the following structure:

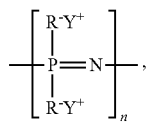

(Structure I)

wherein
Y⁺ is independently at each occurance in the polyphosphazene is an cationic group selected from the group consisting of H⁺, Na⁺, K⁺, Ca²⁺, N-protonated spermine groups, N-protonated spermidine groups, N-protonated imidazoquinoline groups, N-protonated substituted imidazoquinoline groups, N- and/or S-protonated thiaimidazoquinoline groups, and N- and/or S-protonated substituted thiaimidazoquinoline groups,
with the proviso that at least one of the Y⁺ groups is a N-protonated imidazoquinoline group, N-protonated substituted imidazoquinoline group, N- and/or S-protonated thiaimidazoquinoline group, or a N- and/or S-protonated substituted thiaimidazoquinoline group,
R⁻ is independently at each occurance in the polyphosphazene an anionic group, and n is an integer from 10 to 500,000.

2. The polyphosphazene of claim 1, wherein R⁻ is selected from the group consisting of carboxylic acid groups, sufonic acid groups, phosphonic acid groups, and deprotonated forms thereof.

3. The polyphosphazene of claim 1, wherein one or more Y⁺ is:

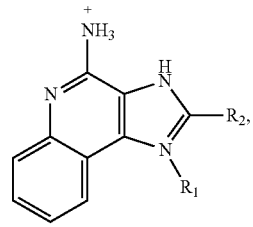

wherein
$R_1$ is independently at each occurance in the polyphosphazene is —H,

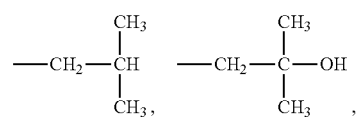

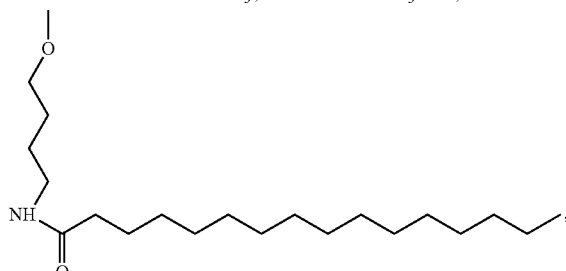

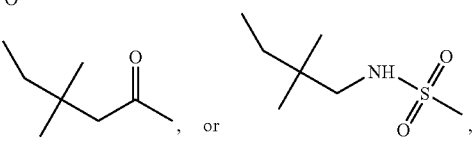

and
$R_2$ is independently at each occurance in the polyphosphazene is —H, —CH₃, —CH₂—CH₂—CH₃,

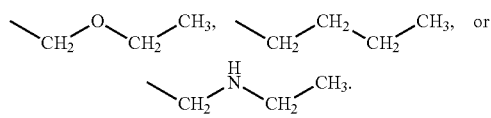

4. The polyphosphazene of claim 3, wherein one or more Y⁺ is:

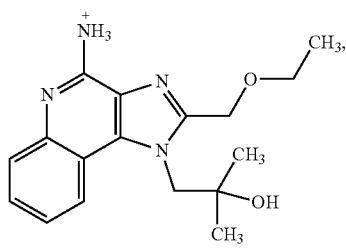

-continued

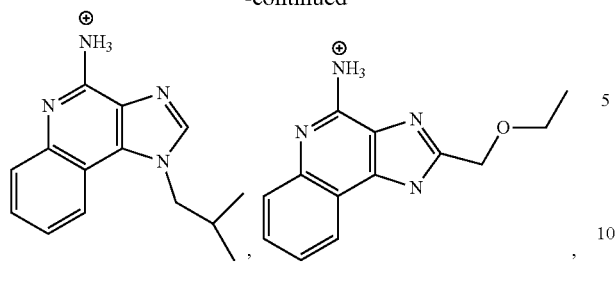

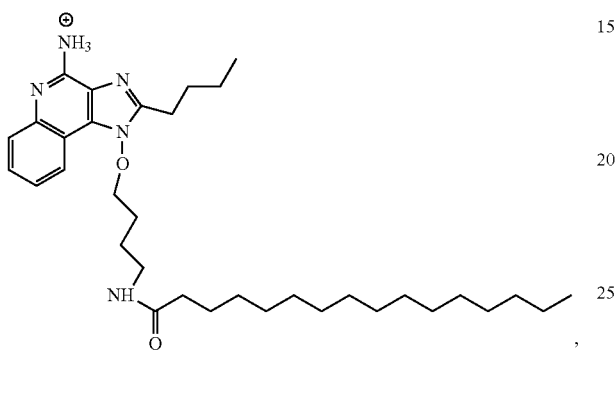

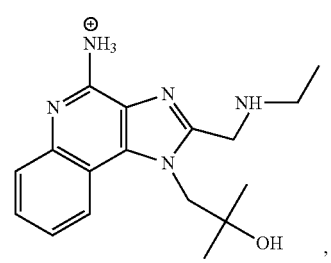

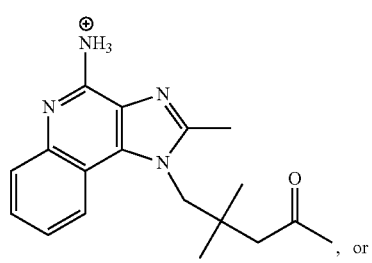

, or

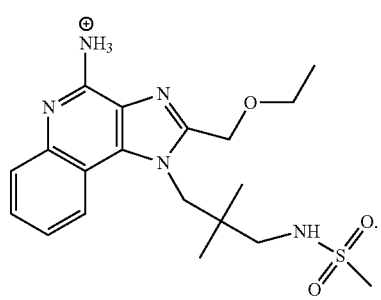

5. The polyphosphazene of claim 1, wherein R⁻ is

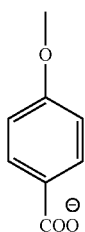

and Y⁺ is

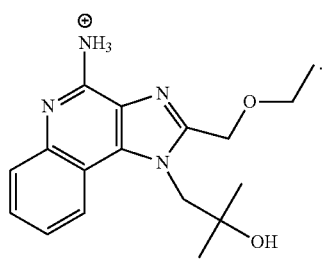 [SMILES: CCOCc1nc2c([NH3+])nc3ccccc3c2n1CC(C)(C)O]

,

6. The polyphosphazene of claim 1, wherein the polyphosphazene has the following structure:

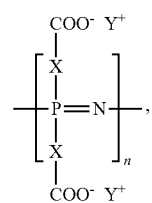

wherein

X is independently at each occurance in the polymer a linking moiety.

7. The polyphosphazene of claim 6, wherein in the linking moiety has independently at each occurance one of the following structures:

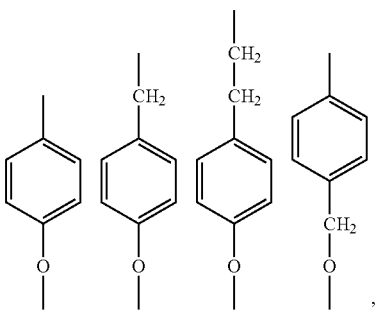

, or

8. The polyphosphazene of claim 1, wherein the polyphosphazene has one of the following structures:

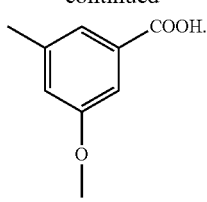

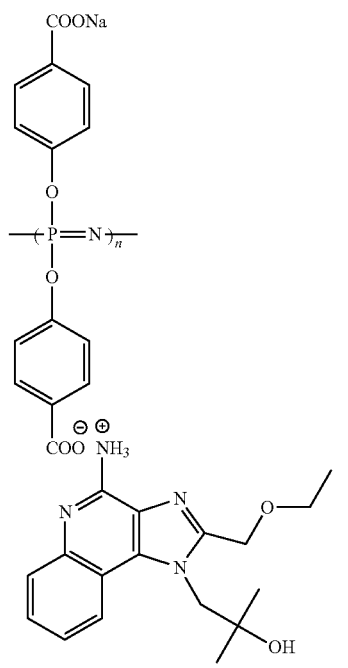 or 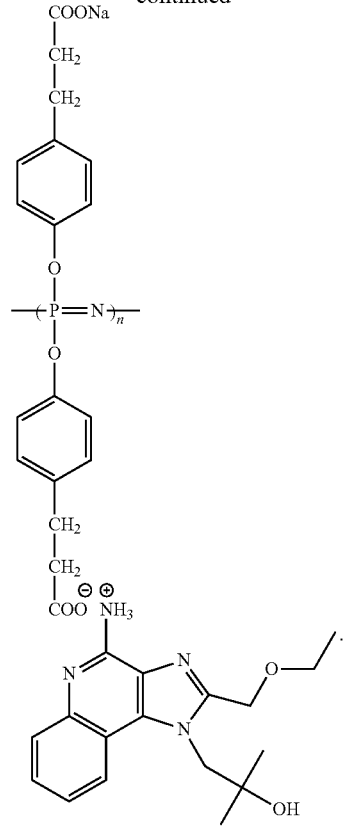

9. A composition comprising a polyphosphazene of claim 1.

10. The composition of claim 9, wherein the composition further comprises a pharmaceutically acceptable carrier.

11. The composition of claim 9, wherein the composition comprises a polyphosphazene, vaccine antigen and, optionally, a pharmaceutically acceptable carrier.

12. The composition of claim 9, wherein the composition comprises a polyphosphazene, an immunomodulating compound and/or TLR agonist, and, optionally, a pharmaceutically acceptable carrier.

* * * * *